US010808035B2

(12) United States Patent
Chmielewski et al.

(10) Patent No.: US 10,808,035 B2
(45) Date of Patent: *Oct. 20, 2020

(54) ANTI CD30 CHIMERIC ANTIGEN RECEPTOR AND ITS USE

(71) Applicants: Markus Chmielewski, Cologne (DE); Andreas Hombach, Cologne (DE); Hinrich Abken, Cologne (DE)

(72) Inventors: Markus Chmielewski, Cologne (DE); Andreas Hombach, Cologne (DE); Hinrich Abken, Cologne (DE)

(*) Notice: Subject to any disclaimer, the term of this patent is extended or adjusted under 35 U.S.C. 154(b) by 174 days.

This patent is subject to a terminal disclaimer.

(21) Appl. No.: 14/912,937

(22) PCT Filed: Aug. 26, 2014

(86) PCT No.: PCT/EP2014/068029
§ 371 (c)(1),
(2) Date: Feb. 19, 2016

(87) PCT Pub. No.: WO2015/028444
PCT Pub. Date: Mar. 5, 2015

(65) Prior Publication Data
US 2016/0200824 A1 Jul. 14, 2016

(30) Foreign Application Priority Data

Aug. 26, 2013 (EP) .................... 13181668

(51) Int. Cl.
| A61K 39/395 | (2006.01) |
| C07K 16/28 | (2006.01) |
| C07K 14/725 | (2006.01) |
| A61K 35/17 | (2015.01) |
| C07K 14/705 | (2006.01) |
| A61K 39/00 | (2006.01) |

(52) U.S. Cl.
CPC .......... *C07K 16/2878* (2013.01); *A61K 35/17* (2013.01); *C07K 14/7051* (2013.01); *C07K 14/70521* (2013.01); *A61K 2039/505* (2013.01); *A61K 2039/5158* (2013.01); *A61K 2039/572* (2013.01); *C07K 2317/622* (2013.01); *C07K 2317/64* (2013.01); *C07K 2317/73* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

FOREIGN PATENT DOCUMENTS

DE  196 40 733 A1  4/1998

OTHER PUBLICATIONS

Savoldo et al. (Blood, vol. 110, No. 7, Oct. 1, 2007, pp. 2620-2630). (Year: 2007).*
Epstein-Barr: Scientists decode secrets of a very common virus that can cause cancer, Duke University Medical Center, Dec. 15, 2010 (retrieved from the internet Sep. 25, 2018) (Year: 2010).*
Savoldo et al., "Epstein Barr virus-specific cytotoxic T lymphocytes expressing the anti-CD30zeta artificial T-cell receptor for immunotherapy of Hodgkin disease", Blood, Oct. 1, 2007, pp. 2620-2630, vol. 110, No. 7.
Hombach et al., "An anti-CD30 chimeric receptor that mediates CD3-zeta-independent T-cell activation against Hodgkins lymphom cells in the presence of soluble CD30", Cancer Research, Mar. 15, 1998, pp. 1116-1119, vol. 58, No. 6.
Ridell et al., "Carving the CAR", Gene Therapy, 2010, pp. 1191-1192, vol. 17.
Hombach et al., "Characterization of a chimeric T-cell receptor with specificity for the Hodgkin's lymphom-associated CD30 antigen", Journal of Immunotherapy, Nov. 1999, pp. 473-480, vol. 22, No. 6.
Hombach et al., "Adoptive immunotherapy with genetically engineered T cells: modification of the IgG1 Fc 'spacer' domain in the extracellular moiety of chimeric antigen receptors avoids 'off-target' activation and unintended initiation of an innate immune response", Gene Therapy, Oct. 2010, pp. 1206-1213, vol. 17, No. 10.
Kofler et al., "CD28 costimulation impairs the efficacy of a redirected T-cell antitumor attack in the presence of regulatory T cells which can be overcome by preventing lck activation", Molecular Therapy, Apr. 2011, pp. 760-767, vol. 19, No. 4.
Di Stasi et al: "T lymphocytes coexpressing CCR4 and a chimeric antigen receptor targeting CD30 have improved homing and antitumor activity in a Hodgkin tumor model", Blood, vol. 113, No. 25, pp. 6392-6402, Jun. 18, 2009.

* cited by examiner

Primary Examiner — Meera Natarajan
(74) Attorney, Agent, or Firm — W&C IP

(57) ABSTRACT

In a first aspect, the present disclosure relates to genetically modified T-cells having a chimeric antigen receptor for use in adoptive cell therapy for treating CD30+cancer in a subject need thereof. In particular, the present disclosure relates to a T-cell containing a specific chimeric antigen receptor being toxic to CD30+cancer cells while being non-toxic to CD30+non-cancer cells. In a further aspect, the present disclosure relates to a specific chimeric antigen receptor and the nucleic acid molecule encoding the receptor as well vectors and cells containing the same. Finally, the present disclosure relates to the use of the chimeric antigen receptor for use in improving persistence and amplification of lymphocyte containing the same and the use of specific peptides for improving persistence and amplification of genetically modified lymphocytes expressing the same.

10 Claims, 4 Drawing Sheets
Specification includes a Sequence Listing.

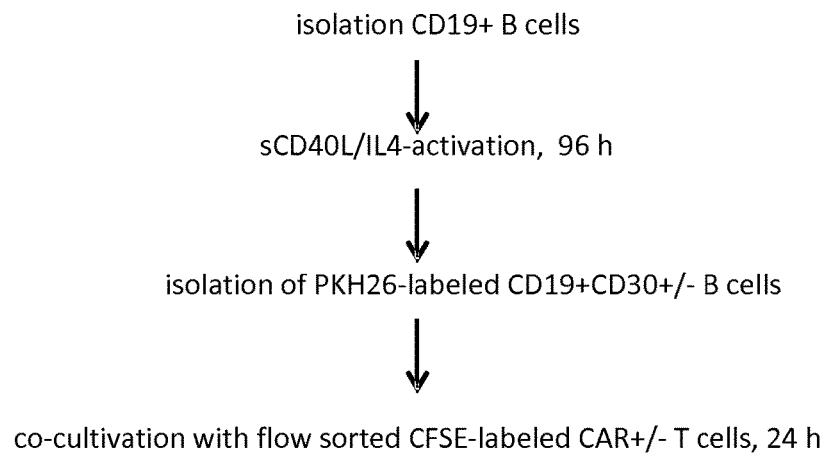
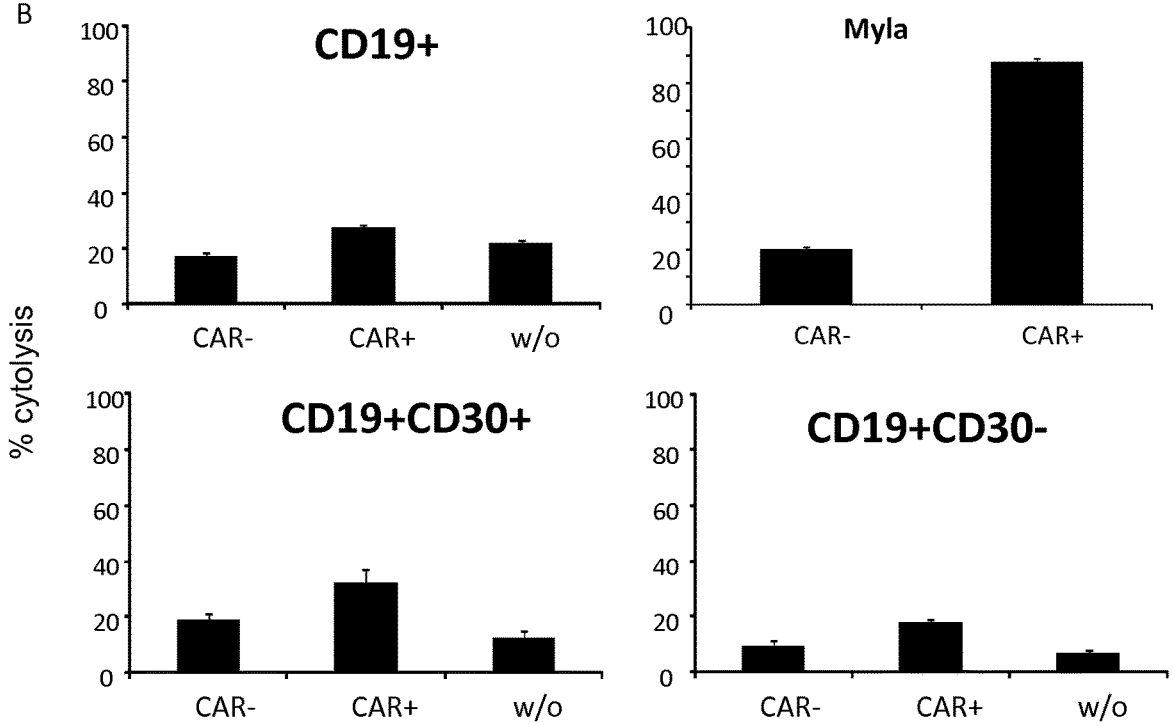
Figure 7 A/B

SEQUENCE LISTING

```
<160> NUMBER OF SEQ ID NOS: 10

<210> SEQ ID NO 1
<211> LENGTH: 756
<212> TYPE: DNA
<213> ORGANISM: human
<220> FEATURE:
<221> NAME/KEY: CDS
<222> LOCATION: (1)..(756)

<400> SEQUENCE: 1 aga atg gcc cag gtg caa ctg cag cag tca ggg gct gag ctg gct aga      48
Arg Met Ala Gln Val Gln Leu Gln Gln Ser Gly Ala Glu Leu Ala Arg
1               5                   10                  15 cct ggg gct tca gtg aag atg tcc tgc aag gct tct ggc tac acc ttt      96
Pro Gly Ala Ser Val Lys Met Ser Cys Lys Ala Ser Gly Tyr Thr Phe
            20                  25                  30 act acc tac aca ata cac tgg gta aga cgg agg cct gga cac gat ctg     144
Thr Thr Tyr Thr Ile His Trp Val Arg Arg Arg Pro Gly His Asp Leu
        35                  40                  45 gaa tgg att gga tac att aat cct agc agt gga tgt tct gac tac aat     192
Glu Trp Ile Gly Tyr Ile Asn Pro Ser Ser Gly Cys Ser Asp Tyr Asn
    50                  55                  60 caa aac ttc aag ggc aag acc aca ttg act gca gac aag tcc tcc aac     240
Gln Asn Phe Lys Gly Lys Thr Thr Leu Thr Ala Asp Lys Ser Ser Asn
65                  70                  75                  80 aca gcc tac atg caa ctg aac agc ctg aca tct gag gac tct gcg gtc     288
Thr Ala Tyr Met Gln Leu Asn Ser Leu Thr Ser Glu Asp Ser Ala Val
                85                  90                  95 tat tac tgt gca aga aga gcg gac tat ggt aac tac gaa tat acc tgg     336
Tyr Tyr Cys Ala Arg Arg Ala Asp Tyr Gly Asn Tyr Glu Tyr Thr Trp
            100                 105                 110 ttt gct tac tgg ggc caa ggg acc acg gtc acc gtc tcc tca agt gga     384
Phe Ala Tyr Trp Gly Gln Gly Thr Thr Val Thr Val Ser Ser Ser Gly
        115                 120                 125 ggc ggt tca ggt gga ggt ggc tct ggc ggt ggc gga tcg gtc atc gag     432
Gly Gly Ser Gly Gly Gly Gly Ser Gly Gly Gly Gly Ser Val Ile Glu
    130                 135                 140 ctc act cag tct cca aaa ttc atg tcc aca tca gta gga gac agg gtc     480
Leu Thr Gln Ser Pro Lys Phe Met Ser Thr Ser Val Gly Asp Arg Val
145                 150                 155                 160 aac gtc acc tac aag gcc agt cag aat gtg ggt act aat gta gcc tgg     528
Asn Val Thr Tyr Lys Ala Ser Gln Asn Val Gly Thr Asn Val Ala Trp
                165                 170                 175 ttt caa caa aaa cca ggg caa tct cct aaa gtt ctg att tac tcg gca     576
```

```
Phe Gln Gln Lys Pro Gly Gln Ser Pro Lys Val Leu Ile Tyr Ser Ala
                180                 185                 190 tct tac cga tac agt gga gtc cct gat cgc ttc aca ggc agt gga tct      624
Ser Tyr Arg Tyr Ser Gly Val Pro Asp Arg Phe Thr Gly Ser Gly Ser
            195                 200                 205 gga aca gat ttc act ctc acc atc agc aat gtg cag tct gaa gac ttg      672
Gly Thr Asp Phe Thr Leu Thr Ile Ser Asn Val Gln Ser Glu Asp Leu
210                 215                 220 gca gag tat ttc tgt cag caa tat cac acc tat cct ctc acg ttc gga      720
Ala Glu Tyr Phe Cys Gln Gln Tyr His Thr Tyr Pro Leu Thr Phe Gly
225                 230                 235                 240 ggg ggc acc aag ctg gaa atc aaa cgg tcg gat ccc                      756
Gly Gly Thr Lys Leu Glu Ile Lys Arg Ser Asp Pro
            245                 250
```

<210> SEQ ID NO 2
<211> LENGTH: 252
<212> TYPE: PRT
<213> ORGANISM: human

<400> SEQUENCE: 2

```
Arg Met Ala Gln Val Gln Leu Gln Gln Ser Gly Ala Glu Leu Ala Arg
1               5                   10                  15

Pro Gly Ala Ser Val Lys Met Ser Cys Lys Ala Ser Gly Tyr Thr Phe
            20                  25                  30

Thr Thr Tyr Thr Ile His Trp Val Arg Arg Pro Gly His Asp Leu
        35                  40                  45

Glu Trp Ile Gly Tyr Ile Asn Pro Ser Ser Gly Cys Ser Asp Tyr Asn
50                  55                  60

Gln Asn Phe Lys Gly Lys Thr Thr Leu Thr Ala Asp Lys Ser Ser Asn
65                  70                  75                  80

Thr Ala Tyr Met Gln Leu Asn Ser Leu Thr Ser Glu Asp Ser Ala Val
                85                  90                  95

Tyr Tyr Cys Ala Arg Arg Ala Asp Tyr Gly Asn Tyr Glu Tyr Thr Trp
            100                 105                 110

Phe Ala Tyr Trp Gly Gln Gly Thr Thr Val Thr Val Ser Ser Ser Gly
        115                 120                 125

Gly Gly Ser Gly Gly Gly Gly Ser Gly Gly Gly Gly Ser Val Ile Glu
130                 135                 140

Leu Thr Gln Ser Pro Lys Phe Met Ser Thr Ser Val Gly Asp Arg Val
145                 150                 155                 160

Asn Val Thr Tyr Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Lys Arg Ser Asp Pro
                245                 250
```

<210> SEQ ID NO 3
<211> LENGTH: 690
<212> TYPE: PRT

<213> ORGANISM: artificial sequence
<220> FEATURE:
<223> OTHER INFORMATION: fusion polypeptide

<400> SEQUENCE: 3

```
Met Asp Phe Gln Val Gln Ile Phe Ser Phe Leu Leu Ile Ser Ala Ser
1               5                   10                  15

Val Ile Met Ser Arg Met Ala Gln Val Gln Leu Gln Gln Ser Gly Ala
            20                  25                  30

Glu Leu Ala Arg Pro Gly Ala Ser Val Lys Met Ser Cys Lys Ala Ser
        35                  40                  45

Gly Tyr Thr Phe Thr Thr Tyr Thr Ile His Trp Val Arg Arg Arg Pro
    50                  55                  60

Gly His Asp Leu Glu Trp Ile Gly Tyr Ile Asn Pro Ser Ser Gly Cys
65                  70                  75                  80

Ser Asp Tyr Asn Gln Asn Phe Lys Gly Lys Thr Thr Leu Thr Ala Asp
                85                  90                  95

Lys Ser Ser Asn Thr Ala Tyr Met Gln Leu Asn Ser Leu Thr Ser Glu
            100                 105                 110

Asp Ser Ala Val Tyr Tyr Cys Ala Arg Arg Ala Asp Tyr Gly Asn Tyr
        115                 120                 125

Glu Tyr Thr Trp Phe Ala Tyr Trp Gly Gln Gly Thr Thr Val Thr Val
    130                 135                 140

Ser Ser Ser Gly Gly Gly Ser Gly Gly Gly Gly Ser Gly Gly Gly Gly
145                 150                 155                 160

Ser Val Ile Glu Leu Thr Gln Ser Pro Lys Phe Met Ser Thr Ser Val
                165                 170                 175

Gly Asp Arg Val Asn Val Thr Tyr Lys Ala Ser Gln Asn Val Gly Thr
            180                 185                 190

Asn Val Ala Trp Phe Gln Gln Lys Pro Gly Gln Ser Pro Lys Val Leu
        195                 200                 205

Ile Tyr Ser Ala Ser Tyr Arg Tyr Ser Gly Val Pro Asp Arg Phe Thr
    210                 215                 220

Gly Ser Gly Ser Gly Thr Asp Phe Thr Leu Thr Ile Ser Asn Val Gln
225                 230                 235                 240

Ser Glu Asp Leu Ala Glu Tyr Phe Cys Gln Gln Tyr His Thr Tyr Pro
                245                 250                 255

Leu Thr Phe Gly Gly Gly Thr Lys Leu Glu Ile Lys Arg Ser Asp Pro
            260                 265                 270

Ala Glu Pro Lys Ser Pro Asp Lys Thr His Thr Cys Pro Pro Cys Pro
        275                 280                 285

Ala Pro Pro Val Ala Gly Pro Ser Val Phe Leu Phe Pro Pro Lys Pro
    290                 295                 300

Lys Asp Thr Leu Met Ile Ala Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
```

```
385             390             395             400
Arg Glu Pro Gln Val Tyr Thr Leu Pro Pro Ser Arg Asp Glu Leu Thr
                    405             410             415
Lys Asn Gln Val Ser Leu Thr Cys Leu Val Lys Gly Phe Tyr Pro Ser
            420             425             430
Asp Ile Ala Val Glu Trp Glu Ser Asn Gly Gln Pro Glu Asn Asn Tyr
        435             440             445
Lys Thr Thr Pro Pro Val Leu Asp Ser Asp Gly Ser Phe Phe Leu Tyr
    450             455             460
Ser Lys Leu Thr Val Asp Lys Ser Arg Trp Gln Gln Gly Asn Val Phe
465             470             475             480
Ser Cys Ser Val Met His Glu Ala Leu His Asn His Tyr Thr Gln Lys
                485             490             495
Ser Leu Ser Leu Ser Pro Gly Lys Lys Asp Pro Lys Phe Trp Val Leu
            500             505             510
Val Val Val Gly Gly Val Leu Ala Cys Tyr Ser Leu Leu Val Thr Val
        515             520             525
Ala Phe Ile Ile Phe Trp Val Arg Ser Lys Arg Ser Arg Leu Leu His
    530             535             540
Ser Asp Tyr Met Asn Met Thr Pro Arg Arg Pro Gly Pro Thr Arg Lys
545             550             555             560
His Tyr Gln Ala Tyr Ala Ala Ala Arg Asp Phe Ala Ala Tyr Arg Ser
                565             570             575
Leu Arg Val Lys Phe Ser Arg Ser Ala Asp Ala Pro Ala Tyr Gln Gln
            580             585             590
Gly Gln Asn Gln Leu Tyr Asn Glu Leu Asn Leu Gly Arg Arg Glu Glu
        595             600             605
Tyr Asp Val Leu Asp Lys Arg Arg Gly Arg Asp Pro Glu Met Gly Gly
    610             615             620
Lys Pro Arg Arg Lys Asn Pro Gln Glu Gly Leu Tyr Asn Glu Leu Gln
625             630             635             640
Lys Asp Lys Met Ala Glu Ala Tyr Ser Glu Ile Gly Met Lys Gly Glu
                645             650             655
Arg Arg Arg Gly Lys Gly His Asp Gly Leu Tyr Gln Gly Leu Ser Thr
                660             665             670
Ala Thr Lys Asp Thr Tyr Asp Ala Leu His Met Gln Ala Leu Pro Pro
            675             680             685
Arg Glx
    690

<210> SEQ ID NO 4
<211> LENGTH: 2070
<212> TYPE: DNA
<213> ORGANISM: artificial sequence
<220> FEATURE:
<223> OTHER INFORMATION: nucleic acid encoding fusion peptide CAR 1138

<400> SEQUENCE: 4
atggatttcc aggtgcagat tttcagcttc ctgctaatca gtgcctcagt cataatgtct    60
agaatggccc aggtgcaact gcagcagtca ggggctgagc tggctagacc tggggcttca   120
gtgaagatgt cctgcaaggc ttctggctac acctttacta cctacacaat acactgggta   180
agacggaggc ctggacacga tctggaatgg attggataca ttaatcctag cagtggatgt   240
tctgactaca atcaaaactt caagggcaag accacattga ctgcagacaa gtcctccaac   300
```

-continued

```
acagcctaca tgcaactgaa cagcctgaca tctgaggact ctgcggtcta ttactgtgca    360
agaagagcgg actatggtaa ctacgaatat acctggtttg cttactgggg ccaagggacc    420
acggtcaccg tctcctcaag tggaggcggt tcaggtggag gtggctctgg cggtggcgga    480
tcggtcatcg agctcactca gtctccaaaa ttcatgtcca catcagtagg agacagggtc    540
aacgtcacct acaaggccag tcagaatgtg ggtactaatg tagcctggtt tcaacaaaaa    600
ccagggcaat ctcctaaagt tctgatttac tcggcatctt accgatacag tggagtccct    660
gatcgcttca caggcagtgg atctggaaca gatttcactc tcaccatcag caatgtgcag    720
tctgaagact ggcagagta ttctgtcag caatatcaca cctatcctct cacgttcgga     780
gggggcacca agctggaaat caaacggtcg gatcccgccg agcccaaatc tcctgacaaa    840
actcacacat gcccaccgtg cccagcacct ccagtcgcgg accgtcagt cttcctcttc      900 cccccaaaac ccaaggacac cctcatgatc gcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtc   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat cccagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggta aaaaagatcc caaattttgg gtgctggtgg tggttggtgg agtcctggct   1560
tgctatagct tgctagtaac agtggccttt attattttct gggtgaggag taagaggagc   1620
aggctcctgc acagtgacta catgaacatg actccccgcc gccccgggcc cacccgcaag   1680
cattaccagg cctatgccgc cgcacgcgac ttcgcagcct atcgctccct gagagtgaag   1740
ttcagcagga gcgcagacgc ccccgcgtac cagcagggcc agaaccagct ctataccgag   1800
ctcaatctag gacgaagaga ggagtacgat gttttggaca gagacgtgg ccgggaccct    1860 gagatggggg gaaagccgag aaggaagaac cctcaggaag gcctgtacaa tgacctgcag   1920
aaagataaga tggcggaggc ctacagtgag attgggatga aggcgagcg ccggaggggc    1980 aaggggcacg atggccttta ccagggtctc agtacagcca ccaaggacac ctacgacgcc   2040
cttcacatgc aggccctgcc ccctcgctaa                                     2070
```

<210> SEQ ID NO 5
<211> LENGTH: 693
<212> TYPE: DNA
<213> ORGANISM: artificial
<220> FEATURE:
<223> OTHER INFORMATION: synthetic nucleic acid sequence

<400> SEQUENCE: 5

```
gagcccaaat ctcctgacaa aactcacaca tgcccaccgt gcccagcacc tccagtcgcg     60
ggaccgtcag tcttcctctt ccccccaaaa cccaaggaca cctcatgat cgcccggacc    120 cctgaggtca catgcgtggt ggtggacgtg agccacgaag accctgaggt caagttcaac    180
tggtacgtgg acggcgtgga ggtgcataat gccaagacaa agccgcggga ggagcagtac    240
aacagcacgt accgtgtggt cagcgtcctc accgtcctgc accaggactg gctgaatggc    300
```

```
aaggagtaca agtgcaaggt ctccaacaaa gccctccag ccccatcga gaaaaccatc    360 tccaaagcca aagggcagcc ccgagaacca caggtgtaca ccctgccccc atcccgggat    420
gagctgacca agaaccaggt cagcctgacc tgcctggtca aaggcttcta tcccagcgac    480
atcgccgtgg agtgggagag caatgggcag ccggagaaca actacaagac cacgcctccc    540
gtgctggact ccgacggctc cttcttcctc tacagcaagc tcaccgtgga caagagcagg    600
tggcagcagg ggaacgtctt ctcatgctcc gtgatgcatg aggctctgca caaccactac    660
acgcagaaga gcctctccct gtctccgggt aaa                                 693

<210> SEQ ID NO 6
<211> LENGTH: 204
<212> TYPE: DNA
<213> ORGANISM: artificial
<220> FEATURE:
<223> OTHER INFORMATION: synthetic sequence

<400> SEQUENCE: 6
ttttgggtgc tggtggtggt tggtggagtc ctggcttgct atagcttgct agtaacagtg    60
gcctttatta ttttctgggt gaggagtaag aggagcaggc tcctgcacag tgactacatg    120
aacatgactc cccgccgccc cgggcccacc cgcaagcatt accaggccta tgccgccgca    180
cgcgacttcg cagcctatcg ctcc                                           204

<210> SEQ ID NO 7
<211> LENGTH: 342
<212> TYPE: DNA
<213> ORGANISM: artificial
<220> FEATURE:
<223> OTHER INFORMATION: synthetic sequence

<400> SEQUENCE: 7
ctgagagtga agttcagcag gagcgcagac gcccccgcgt accagcaggg ccagaaccag    60
ctctataccg agctcaatct aggacgaaga gaggagtacg atgttttgga caagagacgt    120
ggccgggacc ctgagatggg gggaaagccg agaaggaaga accctcagga aggcctgtac    180
aatgacctgc agaaagataa gatggcggag gcctacagtg agattgggat gaaaggcgag    240
cgccggaggg gcaaggggca cgatggcctt taccagggtc tcagtacagc caccaaggac    300
acctacgacg cccttcacat gcaggccctg ccccctcgct aa                       342

<210> SEQ ID NO 8
<211> LENGTH: 198
<212> TYPE: DNA
<213> ORGANISM: artificial
<220> FEATURE:
<223> OTHER INFORMATION: synthetic sequence

<400> SEQUENCE: 8
cctcagctct gctatatcct ggatgccatc ctgtttctgt atggaattgt cctcaccctc    60
ctctactgtc gactgaagat ccaagtgcga aaggcagcta taaccagcta tgagaaatca    120
gatggtgttt acacgggcct gagcaccagg aaccaggaga cttacgagac tctgaagcat    180
gagaaaccac cacagtag                                                  198

<210> SEQ ID NO 9
<211> LENGTH: 25
<212> TYPE: PRT
<213> ORGANISM: artificial
<220> FEATURE:
```

```
<223> OTHER INFORMATION: synthetic peptide
<220> FEATURE:
<221> NAME/KEY: MISC_FEATURE
<222> LOCATION: (8)..(20)
<223> OTHER INFORMATION: SVFLFPPKPKDTL

<400> SEQUENCE: 9

Pro Glu Leu Leu Gly Gly Pro Xaa Xaa Xaa Xaa Xaa Xaa Xaa Xaa Xaa
1               5                  10                  15

Xaa Xaa Xaa Xaa Met Ile Ser Arg Thr
            20                  25

<210> SEQ ID NO 10
<211> LENGTH: 24
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (7)..(19)
<223> OTHER INFORMATION: SVFLFPPKPKDTL

<400> SEQUENCE: 10

Pro Pro Val Ala Gly Pro Xaa Xaa Xaa Xaa Xaa Xaa Xaa Xaa Xaa
1               5                  10                  15

Xaa Xaa Xaa Met Ile Ala Arg Thr
            20
```

ANTI CD30 CHIMERIC ANTIGEN RECEPTOR AND ITS USE

In a first aspect, the present invention relates to genetically modified T-cells having a chimeric antigen receptor (CAR) for use in adaptive cell therapy for treating CD30$^+$ cancer in a subject in need thereof. In particular, the present invention relates to a genetically engineered T-cell containing and expressing a specific chimeric antigen receptor being toxic to CD30$^+$ cancer cells while being non-toxic to CD30$^+$ non-cancer cells. In a further aspect, the present invention relates to a specific chimeric antigen receptor and the nucleic acid molecule encoding the same as well as vectors and cells containing the same. Finally, the present invention relates to the use of a chimeric antigen receptor for use in improving persistence and amplification of lymphocytes containing the same and the use of specific peptides for improving persistence and proliferation of genetically modified lymphocytes expressing the same.

PRIOR ART

Adaptive T-cell transfer has shown significant efficacy in the treatment of malignancies and can be curative in patients with various diseases including leukaemia. Usually, patient derived T-cells are engineered ex vivo to express a recombinant T-cell (TCR), alternatively, a Chimeric Antigen Receptor (CAR). Said Chimeric Antigen Receptor is typically composed of an extracellular antigen binding domain derived from an antibody and an intracellular T-cell activation domain derived from a signaling T-cell receptor endodomain. In contrast to the physiological TCR, the CAR is composed of one single polypeptide chain that combines antigen binding via the extracellular moiety with a T-cell activation machinery provided by the intracellular signalling moiety. Thus, due to the antibody derived binding domain, CAR modified T-cells recognize their target, usually, a cell surface antigen, independently of presentation by the Major Histocompatibility Complex (MHC) and are not compromised by tumour cell variants with lowered or deficient antigen possessing which represents a commonly observed mechanism of tumour immune escape.

CARs are in the focus of extensive research activities during the recent years. In particular, the CAR T-cell cytolytic capacity are in the focus of adaptive cell therapy. Recent clinical trials to treat cancer have underscored the potential of adaptive therapy with CAR-redirected T-cells. For example, neuroblastoma patients treated with GD2 Ganglioside-specific CAR T-cells showed some encouraging anti-tumour effects although the T-cells persisted only for a brief period. Further studies proved the concept that CAR engineered T-cells can initiate a productive anti-tumour response in patients suffering from chronic and acute lymphocytic leukemia. The CAR T-cell approach differs to other antibody mediated immune therapy strategies, e.g. by using immunotoxins, in so far that engineered cells are used instead of single molecules.

In recent years, efforts have been done in the optimization of the CAR design, see e.g. Bridgeman J. S., et al., Curr Gene Ther 2010, 10, 77-90. However, many challenges remain, in particular, the necessity of a more effected anti-tumour response and prolonging T-cell survival allowing long term T-cell persistence of said engineered T-cells in the body. In addition, the co-stimulatory signals required for sustaining T-cell persistence and activation during clinical application remain to be identified. Hence, there is ongoing work on optimizing CAR for various approaches including adaptive immunotherapy.

Already in 1999, Hombach A., et al., J. Immunotherapy, 1999, 22(6), 473-480, describe a chimeric T-cell receptor with specificity for the Hodgkin's lymphoma associated CD30 antigen. It is identified herein, that specific crosslinking of the chimeric receptor induces MHC-unrestricted cellular toxicity against CD30+ target cells but not against CD30− cells. Since CD30 is expressed not only by tumor cells but also by normal activated B-cells, it was hesitated to use CD30 as a target. The assumption was sustained by the report by Savoldo et al., Blood, 2007, 110(7), 2620-2630, which demonstrates that CAR T-cells exhibit increased cytolysis of benign B-cell type lymphoblastoid cell lines (LCL cell lines). The CAR used therein is a "first generation" CAR without an intracellular CD28 domain.

Hombach A. et al., Gene Therapy, 2010, 17, 1206-1213 describe the modification of the IgG1 Fc spacer domain in the extracellular CAR moiety of avoiding off-target activation by Fc receptor$^+$ cells and unintended initiation of an innate immune response.

In Kofler et al., 2011, Mol. Ther. 19, 760-767 a CAR molecule is described having a CD28 endodomain combined with a CD3zeta endodomain and an antibody derived scFv ectodomain specific for CEA. It is described therein that a deletion of the lck binding moiety in the CD28 CAR endodomain improves redirected anti-tumour activity in the presence of T-regulatory (Treg) cells without impairment of interferon-gamma secretion, proliferation and cytolysis. It is speculated that the CAR with the modified CD28 endodomain expedite the implementation of adoptive T-cell therapy in patients with a variety of cancer types that are heavily infiltrated by Treg cells.

In addition, a summary of adoptive therapy of cancer with CAR redirected T-cells is provided in Hombach et al., Current Molecular Medicine, 2013, 13(1), 1-10. Therein, the CAR effects are summarized including co-stimulation activity as well as improvement and prolongation of the redirected anti-tumour T-cell response. In addition, the adverse effects of this kind of adaptive therapy are described including "cytokine storm" and "T-cell repression".

Beside the beneficial effect of the CAR expressing T-cells in adoptive therapy, adverse side effects are known which presently hinder favourite development of respective therapy as mentioned above. As described in the referenced documents, development of CARs result in second and third generation CARs, which harbor one or two costimulatory signaling domains, trying to overcome the same. However, a remaining problem of CAR based adoptive therapy is that the engineered T-cells expressing the CAR do not discriminate between malignant cancer cells (tumor cells) and healthy cells (non-tumor cells). Hence, a major problem of cancer-specific CAR T-cell therapy is to minimize side effects on healthy tissues. Since the anti-tumor effect requires the presence of CAR T-cells in the long-term, it is additionally desired to improve persistence, survival and proliferation of the CAR T-cells.

BRIEF DESCRIPTION OF THE PRESENT INVENTION

In a first aspect, the present invention relates to a T-cell with a chimeric antigen receptor for use in adoptive cell therapy for treating CD30$^+$ cancer, including CD30$^+$ leukemia or CD30$^+$ lymphoma in a subject in need thereof whereby the chimeric antigen receptor contains the following domains starting from the N-terminus to the C-terminus: an anti CD30 single chain antibody domain, in particular, HRS3-scFv of SEQ ID No. 2 or a homolog thereof binding specifically to CD30 having at least 70% identity with SEQ ID No. 2; a spacer domain; a transmembrane domain; and a cytoplasmatic signalling domain; characterized in that said T-cell with the chimeric antigen receptor is toxic to $CD30^+$ cancer cells, in particular, $CD30^+$ leukaemia cells or $CD30^+$ lymphoma cells while being non-toxic to $CD30^+$ non-tumor (healthy) cells in said subject.

In particular, the present invention relates to a T-cell expressing the CAR which is a polypeptide of SEQ. ID No. 3 encoded by a nucleic acid of Seq. ID. No. 4 or homologs thereof.

In a further aspect, the present invention relates to the use of said T-cell with a chimeric antigen receptor according to the present invention for treating $CD30^+$ cancer in a subject in need thereof. In particular, the $CD30^+$ cancer is any one of Hodgkin's lymphoma, anaplastic large cell lymphoma, acute lymphocytic leukaemia, cutaneous lymphoma, mycosis fungoides, Sezary lymphoma, lymphoproliferative diseases, systemic mastocytosis, teratocarcinoma, stem cell derived malignancies, cancer stem cells or others.

Moreover, the present invention relates to a polypeptide of SEQ ID No. 3 or a homolog thereof having at least 90% identity with Seq. ID. No. 3 whereby said polypeptide or a homolog thereof when being expressed in a T-cell as a chimeric antigen receptor displays a toxic effect on $CD30^+$ cancer cells while being non-toxic on $CD30^+$ non-cancer cells.

In addition, the present invention relates to a nucleic acid molecule encoding the polypeptide according to the present invention as well as a vector comprising said nucleic acid sequence, e.g. Seq. ID. No. 4. Moreover, a cell, cell line or host cell containing said nucleic acid sequence or said vector is provided as well as a kit or system containing the vector or a cell, cell line or a host cell containing said vector or said nucleic acid molecule or containing said nucleic acid molecule.

Finally, the present invention relates to the use of the CAR according to the present invention to improve persistence and amplification of any genetically engineered immune cell, in particular lymphocyte, expressing said CAR. In addition, the use of a HRS3 scFv peptide or the nucleic acid encoding the same improving persistence and amplification of any genetically engineered lymphocyte expressing said peptide when said peptide is fused to a chimeric antigen receptor of any other specificity expressed by the genetically engineered lymphocyte.

BRIEF DESCRIPTION OF THE DRAWINGS

FIG. 7: FIG. 7a shows a flow chart of the experimental design. In FIG. 7b target cell lysis of autologous B-cells by anti-CD30 CAR T-cells according to the present invention is shown.

DETAILED DESCRIPTION OF THE PRESENT INVENTION

Figure 1:
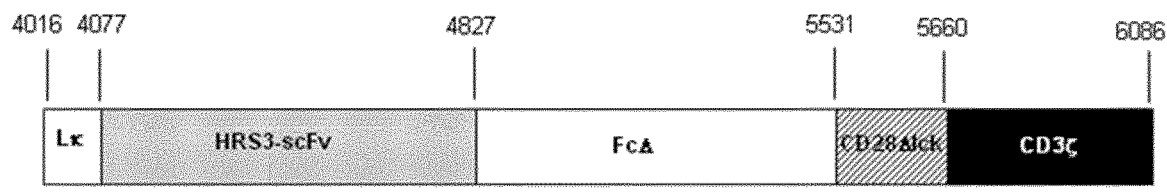
FIG. 1: Modular composition of the molecule CAR #1138 with Seq. ID. No. 3 encoded by a nucleic acid of Seq. ID. No. 4.

The inventors aim to provide genetically engineered T-cells containing a chimeric antigen receptor whereby said T-cells display a toxic activity on $CD30^+$ cancer cells while being non-toxic to $CD30^+$ non-cancer cells in said subject. That is, in a first aspect, the present invention relates to T-cells with a chimeric antigen receptor for use in adoptive cell therapy for treating $CD30^+$ cancer in particular, $CD30^+$ lymphoma or $CD30^+$ leukaemia cells in a subject in need thereof whereby the chimeric antigen receptor contains at least the following domains starting from the N-terminus to the C-terminus: an anti-CD30 single chain antibody domain, in particular, HRS3-scFv of SEQ ID No. 2 or a homolog having binding specificity to CD30 thereof having at least 70% identity with SEQ ID No. 2; optionally a spacer domain; a transmembrane domain; and a cytoplasmatic signalling domain; characterized in that said T-cell with the chimeric antigen receptor is toxic to $CD30^+$ cancer cells, in particular, CD30⁺ leukaemia cells or CD30⁺ lymphoma cells while, being non-toxic to CD30⁺ non-cancer cells in said subject.

In this connection, the term "CD30⁺ cancer cells" refers to malignant cells or neoplastic cells expressing the CD30 molecule.

Further, the term "CD30⁺ non-cancer cells" refers to benign (healthy) cells expressing the CD30 molecule, like activated T-cells, B-cells or stem cells.

The terms "non-tumor cells" and "tumor cells" as well as "non-cancer cells" and "cancer cells" are used herein interchangeably unless otherwise defined.

As used herein, the term "comprise" or "comprising" as well as the terms "contain" or "containing" refers to the embodiment of "consist" or "consisting".

The term "homolog" as used herein refers to molecules, either DNA or polypeptides, having a sequence homology of a certain amount, namely of at least 70%, like at least 80%, 90%, 95%, 96%, 97%, 98%, 99% of the nucleic acid sequence or the amino acid sequence it is referred to. Homology refers to the magnitude of identity between two sequences. Homolog sequences have the same or similar characteristics, in particular, have the same or similar property of the sequence as identified. For example, the homolog of the HRS3 scFv sequence of Seq. ID. No. 2 has the same or similar binding specificity to the CD30 molecule as it is the case for the HRS3 scFv molecule. Further, homologs include nucleic acid molecules encoding the same peptide but may vary in its sequence due to the degeneracy of the genetic code. Further, identify refers to presence of identical amino acid or nucleic acid molecules in the order as described for the sequence it refers to. That is, in case of at least 90% identity, 90% or more of the nucleic acid and amino acid molecules, respectively, are identical at the respective positions. Unless otherwise identified, the terms "homology" and "identity" are used herein interchangeably. In an embodiment, the homolog is a homolog of the HRS3 scFv peptide of SEQ ID No. 2 binding specifically to the same epitope recognized by the HRS3 scFv peptide of SEQ ID No. 2.

In addition, the term "genetically engineered" refers to cells being manipulated by genetic engineering. That is, the cells contain a heterologous sequence which does not naturally occur in said cells. Typically, the heterologous sequence is introduced via a vector system or other means for introducing nucleic acid molecules into cells including liposomes. The heterologous nucleic acid molecule may be integrated into the genome of said cells or may be present extra-chromosomally, e.g. in the form of plasmids. The term also includes embodiments of introducing genetically engineered, isolated CAR polypeptides into the cell.

Generally, CARs are fusion proteins, consisting of an extracellular antibody type recognition domain fused to intracellular T-cell signalling proteins. Typically, the ectodomain containing the antigen recognition region comprises a signal peptide and an antigen recognition unit. According to the present invention, the ectodomain comprises an anti CD30 single chain domain. It is preferred, that said single chain domain is a single chain domain selected from HRS3 scFv of SEQ. ID. No. 2 or homologs thereof binding specifically to CD30 having at least 70% identity with SEQ ID No. 2. Further, the single chain domain may be derived from other anti-CD30 antibodies like HRS4 or Ki-4. Said antibodies have the same binding specificity to CD30 as it is the case for the HRS3 antibody, namely binding to the same epitope of CD30.

The ectodomain may be spaced apart from the transmembrane domain by the presence of a spacer domain. Said optional spacer domain links the antigen-binding domain to the transmembrane domain and it is preferred that said transmembrane domain is flexible enough to allow the antigen binding domain to orient in different directions to facilitate antigen recognition.

The transmembrane domain is typically a hydrophobic alpha helix that spans the membrane. Other transmembrane domains can also be used. Finally, the endodomain represents the signalling domain in the cytoplasmic part of the CAR.

It has been recognized that a T-cell containing the CAR as described, namely, containing a CAR starting from the N-terminus to the C-terminus having the following composition: an anti-CD30 single chain antibody domain, optionally, a spacer domain, a transmembrane domain, a cytoplasmic domain is able to display toxic activity distinctively between CD30⁺ cancer cells and CD30⁺ non-cancer cells. Thus, the T-cells of the present invention overcome the problems known in the art of cytotoxic effects on both cancer CD30⁺ cells and healthy CD30⁺ cells, e.g. as described in the art.

In an embodiment of the present invention, the CAR comprises a leader sequence being located N-terminally to the anti CD30 single chain antibody domain.

In addition, in another embodiment, the anti-CD30 single chain antibody domain is a HRS3 scFv peptide, in particular, of SEQ. ID. No. 2. It has been recognized herein that an anti-CD30 single chain antibody fragment of the variable region (scFv), in particular, of HRS3, allows to display the desired activity, namely, being toxic to CD30⁺ cancer cells while being non-toxic to CD30⁺ non-cancer cells.

In another embodiment, the spacer domain of the CAR molecule is an IgG₁ hinge-CH2CH3 domain of SEQ. ID. No. 5 or homologs thereof having at least 70% identity therewith, preferably, the spacer domain is a mutated IgG₁ hinge-CH2CH3 domain according to SEQ. ID. No. 5.

In some embodiments, between the spacer domain and the transmembrane domain a linker may be located. For example, in the CAR of Seq. ID. No. 3 a linker of 4 amino acids is located between the spacer domain and the transmembrane domain.

Further, another embodiment relates to a T-cell with a chimeric antigen receptor wherein the transmembrane domain is derived from the CD28 molecule, e.g. the transmembrane domain of the CD28 molecule lacking the lck domain of SEQ. ID. No. 6

The signalling domain or endodomain or intracellular domain which are used herein interchangeably, contains a CD3 zeta or FcEpsilon receptor (IgE receptor) gamma chain signalling chain or a co-stimulatory domain. For example, the intracellular domain is a CD3 zeta signalling domain of SEQ. ID. No. 7 or a homolog thereof having at least 70% homology. In another embodiment, the intracellular domain is the Fc epsilon receptor gamma signalling domain of SEQ. ID. No. 8 or a homolog thereof having at least 70% identity. The signalling domain is responsible for the activation of the cytotoxic activity in T-cells or interferon-gamma secretion by T-cells, respectively.

The CAR molecule may be a so-called "second generation" CAR molecule. Second generation CAR molecules have improved signalling domains additionally containing a second signalling domain, e.g. derived from CD28, CD134 (OX40) or CD137 (4-1BB). "Third generation" CAR molecules contain a combined co-stimulatory signalling domain, e.g., CD28 combined with CD137 or CD134.

An overview about the CAR molecules is provided e.g. in Gilham D. E. et al., Trends in Molecular Medicine, 2012, 18(7), 377-384.

In a preferred embodiment of the present invention, the T-cell is a T-cell with a chimeric antigen receptor wherein the chimeric antigen receptor is a polypeptide of SEQ. ID. No. 3. Said CAR is also referred to herein as #1138.

The anti-CD30 CAR #1138 is expressed on the surface of T-cells and is composed in the extracellular part of the anti-CD30 single chain fragment of variable region (scFv) antibody HRS3 and the modified human IgG1 CH2CH3 domain as spacer between scFv and the trans-membrane domain. The modification of the IgG1 domain consists of point mutations to convert the wild-type amino acid sequence PELLGGP $X_{13}$ MISRT (Seq. ID. No. 9) to PPVAGP $X_{13}$ MIART (Seq. ID. No. 10) which reduces unintended binding of the CAR Fc domain to Fc receptors on other cells like innate immune cells which would unintendedly mediate their activation and the activation of the CAR T-cells. The transmembrane and intracellular membrane proximal part of CAR #1138 is derived from human CD28 and is fused to the intracellular part of human CD3zeta. The CD28 sequence is mutated at P560>A560, P563>A563, P564>A564 (Kofler et al., Mol. Ther. 19, 760-767 (2011). Thereby the CD28 binding site for the lck kinase is destroyed with the consequence that activation of the lck signalling pathway and subsequent CAR mediated IL-2 secretion is prevented. Pre-clinical models imply that Treg cell mediated repression of CAR T-cell effector functions is reduced under these conditions.

As demonstrated in the examples, the T-cells (either $CD4^+$ or $CD8^+$ T-cells) act differently on $CD30^+$ cells, namely, $CD30^+$ cancer cells are killed while $CD30^+$ non-cancer cells remain alive in presence of T-cells with #1138 CAR.

As an example, T-cells expressing the #1138 CAR are non toxic against healthy human $CD30^+$ $CD34^+$ hematopoetic stem cells whereas $CD30^+$ lymphoma cells are eliminated.

Moreover, as demonstrated in the example, the T-cells containing the #1138 CAR according to the present invention do not show toxic activity toward healthy human B- and T-cells in a mouse model. No significant autoimmune activity towards autologous healthy cells and no worse side effects occurred. In addition, lymphocyte immune response against pathogens was not altered allowing a cellular immune protection against the tested pathogen.

In a further aspect, the present invention relates to the use of the T-cell with a chimeric antigen receptor according to the present invention in adaptive cell therapy for treating $CD30^+$ cancer in a subject in need thereof. For instance the $CD30^+$ cancer may be Hodgkin's lymphoma, anaplastic large cell lymphoma, acute lymphocytic leukaemia, cutaneous lymphoma, mycosis fungoides, lymphoproliferative diseases, systemic mastocytosis, teratocarcinoma, stem cell derived malignancies, or cancer stem cells or others.

That is, surprisingly T-cells with the chimeric antigen receptor according to the present invention allows to treat $CD30^+$ cancer in a subject in need thereof without harming the non-cancer $CD30^+$ cells present in the subject to be treated. In contrast to previous observations with a tremendous variety of CARs having different antigen binding domains, the anti-CD30 antibody domain allows to eliminate malignant $CD30^+$ cells while benign $CD30^+$ cells are not affected.

In a further aspect, the present invention relates to the polypeptide of SEQ. ID. No. 3 representing the CAR polypeptide denoted #1138 herein, or a homolog thereof having at least 90% identity whereby said polypeptide or its homolog when being expressed in a T-cell is a chimeric antigen receptor displaying a toxic effect on $CD30^+$ cancer cells while being non-toxic on $CD30^+$ non-cancer cells. For example, the polypeptide of Seq. ID. No. 3 is encoded by the nucleic acid sequence of Seq. ID. No. 4.

The polypeptide is composed of the HRS3-scFv single chain domain of anti-CD30 antibody, a spacer domain being a mutated IgG1 hinge-CH2CH3 domain, a transmembrane domain derived from CD28, in particular, a CD28 derived transmembrane domain lacking lck domain, and the intracellular domain of CD3 zeta.

In addition, the present invention provides nucleic acid molecules comprising the nucleic acid sequence encoding the polypeptide according to the present invention. Furthermore, vectors are provided comprising the nucleic acid sequence according to the present invention encoding the polypeptide as described. The skilled person is well aware of suitable vector systems and vectors, in particular, vectors allowing transfection and transduction of eukaryotic cells, in particular, T-cells.

Moreover, the present invention provides a cell, cell line or a host cell containing the vector according to the present invention or a nucleic acid molecule according to the present invention. Preferably, said cell, cell line or host cell is a T-cell, e.g., a $CD4^+$ T-cell or a $CD8^+$ T-cell.

Further, the present invention provides a kit or system containing the vector according to the present invention, the cell, cell line or host cell according to the present invention, or the polypeptide according to the present invention or a nucleic acid molecule according to the present invention or mixtures thereof for use in the production of T-cells expressing the chimeric antigen receptor. The kit or system according to the present invention may contain further components including means for introducing the vector or polypeptide on nucleic acid molecules into the cells. The skilled person is well aware of suitable means for doing so.

Moreover, the present invention relates to a chimeric antigen receptor as defined herein for use to improve persistence and proliferation of any genetically engineered lymphocyte expressing said chimeric antigen receptor #1138 or homologs thereof. That is, the present inventors surprisingly realized that in contrast to the broad variety of other chimeric antigen receptors, the chimeric antigen receptor #1138 according to the present invention confers an improved persistence and amplification of the genetically engineered lymphocytes as demonstrated in the examples. Hence, the clinically relevant shortcoming of so far known CAR T-cells is overcome where the persistence of the engineered T-cells in the subject was too short and the number of engineered T-cells rapidly dropped.

Finally, the present invention provides a HRS3 scFv peptide, and homologs thereof having the same property with respect to the epitope identified by the scFv of HRS3. That is, e.g. the antibodies HRS4 and Ki-4 bind to the same epitope. Thus, scFv of HRS4 and scFv of Ki-4 likely have the same activity with respect to this invention. In addition, nucleic acid sequences encoding the said peptides are provided. Said peptides and nucleic acids are suitable for use to improve persistence and amplification of any genetically engineered lymphocyte expressing said peptide when said scFv peptide is part of a chimeric receptor or fused to a chimeric antigen receptor of any other specificity expressed by the genetically engineered lymphocyte. That is, combining the HRS3 scFv peptide, for example, the HRS3 scFv peptide of SEQ ID No. 2, e.g. encoded by the sequence of Seq. ID. No. 1, with a CAR molecule having additionally a different antigen binding specificity, improves the persistence and amplification of said engineered lymphocytes.

The present invention is further described by way of examples. Said examples illustrate the invention further without limiting the same thereto.

EXAMPLES

Preparation of the Test Item

The retroviral vector coding for the #1138 CAR was produced according to SOP-GL-VectProd using a Galv pseudotyped envelope. In summary vector particle production was done transiently on the human embryonic kidney cell line 293T after Polyfect® mediated DNA transfection. Vector particles were pseudotyped with Galv. No vector titer was determined.

Transduction of human blood lymphocytes was done according to standard techniques (Cheadle, E. J., et al., Chimeric antigen receptors for T-cell based therapy. Chapter 36, in: "Antibody engineering: methods and protocols", 2nd Edition, Ed. P. Chames, Meth. Mol. Biol. 907, 645-666 (2012), doi: 10.1007/978-1-61779-974-7_36). In summary human lymphocytes were transduced with a 2-day supernatant from transfected 293T cells for 2 days. The CAR #1138 was expressed by 20-35% of human T-cells as measured at day 2 by flow cytometry using an antibody directed to the extracellular IgG1 CH2 CH3 domain of the CAR. For comparison the CAR #1175, see Hombach A, et al., Gene Ther. 2010 October; 17(10):1206-13. doi: 10.1038/gt.2010.91. Epub 2010 Jun. 17, was expressed on 17-30% of human T-cells as measured by the same procedure.

$CD4^+$ and $CD8^+$ T-cells which express the CAR #1138 on the cell surface can be recorded by use of the 9G10 antibody which binds specifically the CAR HRS3 scFv domain. T-cells engineered with the #1138 CAR bind specifically to CD30 expressing cells and become activated indicated by increased secretion of cytokines including IFN-γ, by increase in proliferation and in cytolysis of $CD30^+$ target cells. Noteworthy, only background levels of IL-2 are secreted when T-cells are stimulated by the CAR #1138. IL-2, however, is secreted in physiological amounts when T-cells are stimulated by their physiological TCR and CD28. Activation of the T-cells #1138 is antigen-specific as defined by the specificity of the CAR since $CD30^-$ cells do not trigger T-cell activation. Soluble CD30, which accumulates in the serum of $CD30^+$ lymphoma patients, does not block CAR mediated T-cell activation in concentrations up to 10 µg/ml [Hombach A, et al., Cancer Res. 1998 Mar. 15; 58(6)1116-9]. This is due to the fact that the CAR must be cross-linked by binding the multiple copies of the targeted antigen in order to trigger T-cell activation which can only occur when CD30 is immobilized on surfaces or expressed on the surface of target cells but does not occur when the CD30 protein is present in solution.

Example 1: Activity of CAR #1138 Modified T-Cells Toward $CD30^+$ Tumor and Healthy Cells Engineering of T-Cells with CAR #1138

Figure 2:
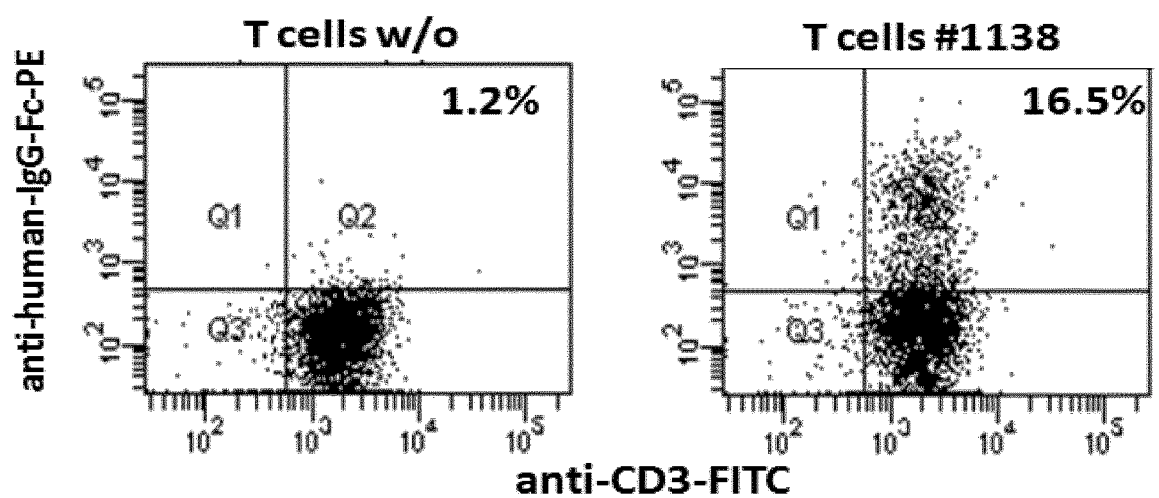
FIG. 2: Engineered human T-cells express the CAR #1138. Human peripheral T-cells were isolated from the blood of a healthy donor and retrovirally engineered by transduction of vector #1138. After 12 hrs cells were tested for #1138 CAR expression by two colour FACS according to SOP_tumorgenetics_FACS using a PE-labelled polyclonal goat anti-human IgG Fc antibody and the FITC-labelled murine anti-human CD3 monoclonal antibody UCHT1.

Engraftment of human peripheral T-cells with the #1138 CAR was assessed by two colour flow cytometry 12 hrs after transduction. FIG. 2 shows a dot blot analysis of CAR engineered T-cells. The number of T-cells with #1138 CAR expression was 16.5% of all T-cells.

Purification of T-Cells with CAR #1138 and Control T-Cells

T-cells #1138 were cultivated for 60 hrs, labelled with the anti-human IgG-Fc-FITC, antibody which binds to the CAR, and the anti-CD3-PE antibody, which identifies the T-cells, and sorted using the FACSAria III cell sorter. Gates were set for $CD3^+$ CAR #1138$^+$ and $CD3^+$ CAR #1138$^-$ T-cells. Aliqouts of sorted cells were re-analyzed by FACS. The purity of $CD3^+$#1138$^+$ and $CD3^+$#1138$^-$ T-cells was 94.4% and 99.6%, respectively.

Isolation of Allogeneic $CD34^+$ Hematopoietic Stem Cells $CD34^+$ cells were isolated from peripheral blood of a volunteer donor upon mobilization with GM-CSF by density centrifugation and magnetic cell sorting (MACS). Cells were labelled with an anti-CD34 PE-conjugated mAb and aliquots of fractionated and unsorted cells were analyzed by FACS. The purity of isolated $CD34^+$ cells was 94.4%.

CFSE-Labeling of Myla Cells

Myla cells were labelled with 1.25 µM CFSE and mixed with isolated $CD34^+$ hematopoietic stem cells. $CD34^+$ cells which were identified by anti-CD34-PE mAb and CFSE$^+$ Myla cells can clearly be discriminated and both populations can separately be analyzed for viability.

Redirected Toxicity of T-Cells with #1138 CAR Towards $CD30^+$ Lymphoma Cells Versus $CD30^+$ $CD34^+$ Hematopoietic Stem Cells.

$CD30^+$ MyLa lymphoma cells together with $CD30^+$ $CD34^+$ healthy hematopoietic stem cells were co-incubated with T-cells engineered with anti-CD30 CAR #1138. As controls same $CD30^+$ cells were co-incubated with T-cells without CAR ("T-cells #1138 negative") derived from the same donor and cell preparation.

Figure 3:
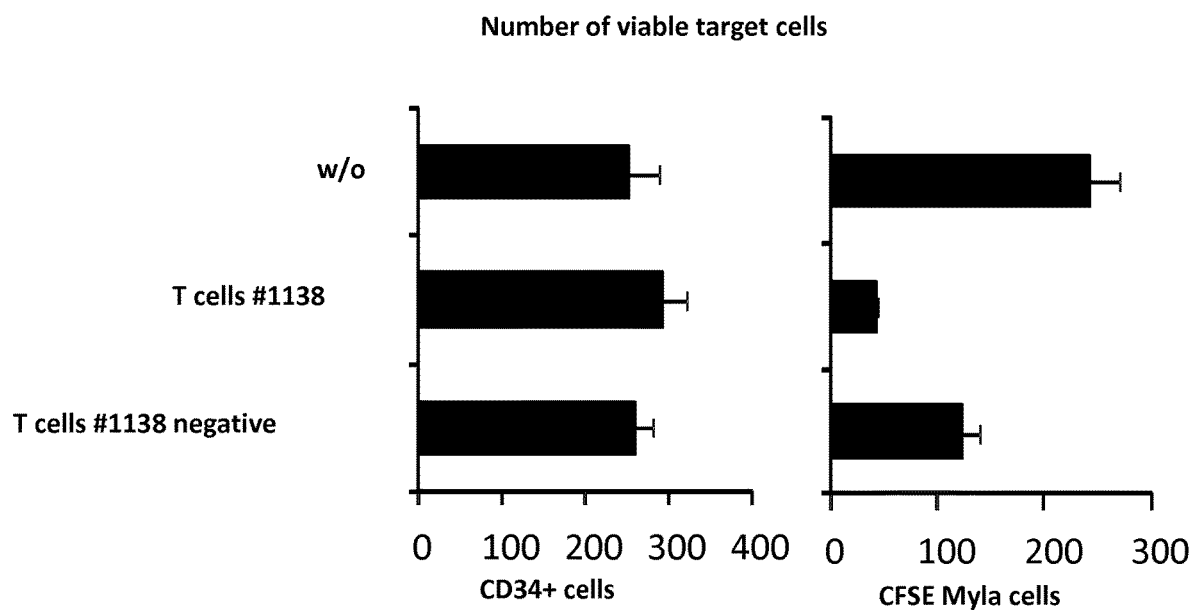
FIG. 3: Engineered T-cells eliminate $CD30^+$ lymphoma cells and less $CD34^+$ $CD30^+$ hematopoietic stem cells. T-cells with CAR #1138, T-cells without CAR after shame-transduction (T-cells #1138 negative) and non-modified T-cells (w/o) were co-cultivated with allogeneic $CD34^+$ hematopoetic stems cells, induced to express CD30, and CFSE-labeled $CD30^+$ Myla cells for 24 hrs. Cells were stained with the anti-CD34-PE monoclonal antibody (mAb) AC136 (20 µl). Counting standard (5 µl/test) and 7 AAD (5 µl/test) were added and cells were analyzed by FACS setting counts for 1,000 events of standard beads. The test was done in triplicates and the total number of target cells was determined.

The total number of target cells was determined by FACS and standardized by using a counting standard. $CD34^+$ $CD30^+$ hematopoietic stem cells were identified by staining with the monoclonal anti-CD34-PE antibody and lack of CSFE label which is different to CFSE-stained Myla cells. The test was done in triplicates and the data are summarized in FIG. 3. The number of $CD34^+$ hematopoietic stem cells does not decrease in presence of T-cells without CAR (w/o), with CAR (T-cells #1138) or in the presence of T-cells lacking the CAR after the transduction procedure (T-cells #1138 negative). In contrast to $CD34^+$ $CD30^+$ healthy cells, the number of $CD30^+$ CFSE-labelled Myla cells substantially decreased due to CAR T-cell mediated killing (T-cells #1138) in addition to the expected allo-reactivity of T-cells (T-cells #1138 negative).

Figure 4:
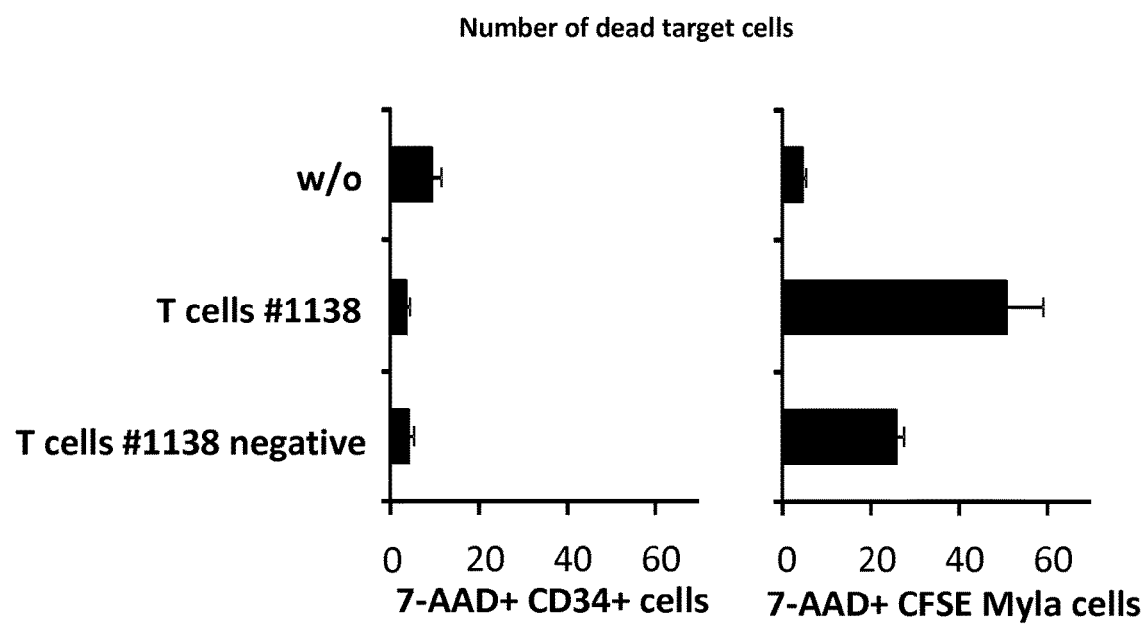
FIG. 4: T-cells with #1138 and without #1138 CAR, respectively, were co-cultivated with allogeneic $CD34^+$ hematopoietic stem cells and CFSE-labeled $CD30^+$ Myla cells for 24 hrs. Cells were stained with the anti-CD34-PE mAb AC136 (20 µl). Counting standard (5 µl/test) and 7-AAD (5 µl/test) were added and cells were analyzed by FACS by setting counts for 1,000 events of standard beads. The number of dead cells ($7-AAD^+$) in each target population was determined and diplayed as % dead cells of total target cells using the following formula: percent of dead target cells=(number of $7-AAD^+$ target cells/number of total target cells)*100. The test was performed in triplicates.

To determine toxicity of T-cells CAR #1138 against $CD30^+$ healthy and tumor cells, the number of dead target cells was determined in a direct fashion by means of flow cytometry. $CD34^+$ $CD30^+$ healthy cells were identified by the anti-CD34-PE antibody and discriminated from CFSE-labelled Myla lymphoma cells. Viable and dead target cells were determined by staining with 7-AAD. Data are summarized in FIG. 4.

CONCLUSIONS

The toxicity of T-cells with the anti-CD30 CAR #1138 against healthy human $CD30^+$ $CD34^+$ hematopoietic stem cells was tested in comparison to targeting $CD30^+$ lymphoma cells. T-cells from a healthy donor were engineered to express the #1138 CAR and T-cells without CAR from the same transduction batch were purified by cell sorting. The procedure was used to compare CAR mediated specific toxicity versus any un-specific toxicity induced by the transduction process itself. We recorded toxicity of purified T-cells #1138 for reactivity towards $CD34^+$ allogeneic hematopoietic stem cells. Moreover, we recorded toxicity against $CD30^+$ lymphoma cells simultaneously to toxicity against $CD30^+$ $CD34^+$ hematopoietic stem cells in the same assay by mixing the differently labelled target cells. The procedure allows to estimate direct and bystander toxicity in the same assay. The observation time for both the test group and the control group was 24 hrs.

We found that the number of CFSE-labelled CD30+ Myla lymphoma cells specifically decreased when co-incubated with T-cells #1138 compared to co-incubation with #1138 negative T-cells. In line with that, the number of dead Myla target cells substantially increased upon co-incubation with T-cells #1138. In contrast, neither the absolute number of CD34+ healthy hematopoietic stem cells decreased nor did increase the number of dead CD34+ cells. Notable, we did not observe any direct or bystander toxicity against CD34+ hematopoietic stem cells although there occurs specific killing of CD30+ tumor cells by T-cells #1138 in the near vicinity of CD34+ CD30+ cells. Taken together T-cells with CAR #1138 did not show toxicity against healthy CD30+ CD34+ hematopoietic stem cells while specific toxicity toward CD30+ lymphoma cells.

Example 2: No Toxic Activity of CAR #1138 Engineered T-Cells Toward Healthy Human B- and T-Cells in a Mouse Model Dose Selection Human CD34+ hematopoietic stem cells were isolated from cord blood. New born Rag2$^{-/-}$ common gamma chain$^{-/-}$ mice were transplanted with 3×10$^5$ CD34+ hematopoietic stem cells to engraft the human hematopoietic system. Successfully engrafted animals were transplanted with 2.5×10$^6$ T-cells per mouse by a single injection into the tail vein.

Animals/Animal Maintenance

Species: Mouse

Strain/Stock: Rag2$^{-/-}$ cγ$^{-/-}$

Selection of species: The T- and B-cell deficient mouse model was used to engraft the human hematopoietic system; the reconstituted hematopoietic system closely mimics the human situation.

Identification of Animals

TABLE 1

| 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|
| A-w1 | A-w2 | A-m1 | B-w1 | B-w2 | B-m1 | C-w1 | C-w2 | C-m1 | C-m3 | D-w1 | D-m1 | D-m1 | D-m2 | E-w1 | W-m1 | E-m2 | E-m3 | E-m4 | E-m5 | E-m6 |

Table 1
A-E = breeding group;
m = male
w = female;
1-6 mouse number

Transplantation of Human Hematopoiesis

Rag2$^{-/-}$ cγ$^{-/-}$ mice were engrafted with isolated human CD34+ hematopoietic stem cells from cord blood (SOP-RepopCD34, Appendix 6) and monitored for successful establishment of mature human lymphocytes after 5 weeks by flow cytometric recording of human CD45+ and CD4+ CD45+ T-cells in the peripheral blood.

Experimental Groups

The animals were allocated to three test groups according to the Study Plan. The following groups were employed.

TABLE 2

| Group 1: | (# 1138 + 9G10) | E-m2 left and right | CD3+ cells, #1138 |
|---|---|---|---|
| | | C-m3 (left) | CD3+ cells, #1138 |
| | | E-m6 (left) | CD3+ cells, #1138 |

TABLE 2-continued

| Group 2: | (#1138) | E-m4 (none) | CD3+ cells, #1138 |
|---|---|---|---|
| | | E-m5 (right) | CD3+ cells, #1138 |
| | | E-w1 (none) | CD3+ cells, # 1138 |
| Group 3: | (# 1175) | B-w1 (none) | CD3+ cells, #1175 |
| | | | CD3+ cells, #1175 |
| | | | CD3+ cells, #1175 |

Adoptive cell therapy of animals with human hematopoiesis: i.v. tail vein injection of CD3+ T-cells with #1138 CAR into Rag2$^{-/-}$ cγ$^{-/-}$ recipient mice with established autologous human hematopoiesis; control: transplantation of CD3+ T-cells with #1175 CAR Engraftment of Human Hematopoietic Cells in Rag2$^{-/-}$ cγ$^{-/-}$ recipient mice.

Engraftment of the human CD34+ hematopoietic stem cell transplant and subsequent establishment of human hematopoiesis in the peripheral blood of mice was assessed by flow cytometric recording of human CD4+ and CD45+ cells 5 weeks after transplantation. The human hematopoietic system engrafted in 12/21 mice indicated by human CD4+CD45+ T-cells in the peripheral blood. Mock-engrafted and non-treated Rag2$^{-/-}$ cγ$^{-/-}$ mice do not harbour these cells. Litter mice A, B, C, D and E were engrafted with the same donor of CD34+ cord blood cells each. Only mice which successfully engrafted were used for adoptive cell therapy.

Expression of CAR #1138 by Engineered Human T-Cells

Human CD3+ T-cells (from the same donor as of the CD34+ cells) were ex vivo engineered to express the CD30-specific CAR #1138 or as control the CEA-specific CAR #1175. CAR #1175 harbors the CEA-specific scFv BW431/26 instead of the CD30-specific scFv HRS3 of CAR #1138 and was used as control throughout the study. CAR expression on human CD3+ T-cells was recorded by flow cytometric detection of both the extracellular human IgG "spacer" domain of the CAR and human CD3.

CAR engineered T-cells were transferred to the corresponding mouse with the autologous hematopoietic system by i.v. injection (2.5×10$^6$ T-cells with CAR per mouse).

Toxicity of T-Cells with #1138 CAR In Vivo

1. Peripheral Blood Counts and Body Weight

No apparent abnormalities were observed in the test group during the observation period. The percentage of lymphocytes (approx. 70%), monocytes (approx. 10%) and granulocytes (approx. 20-25%) in the cellular compartment of the peripheral blood of the test group did not differ from those observed in the control animals which did not receive T-cells or received T-cells with the control CAR #1175.

The number of CD30+ T- and B-cells in the peripheral blood of mice in presence or absence of anti-CD30 T-cells #1138 or anti-CEA T-cells #1175 as control were recorded by flow cytometry on day −5 before T-cell therapy and on day 7, 14, 22, 29, 36, 43, 50 after T-cell therapy.

No alteration in the number of CD30+CD4+ T-cells and CD30+CD19+ B-cells in presence of T-cells #1138 was recorded after adoptive cell therapy during the 7 week observation period compared to day −5 before T-cell therapy. The number of CD30+CD4$^+$ T-cells was the same compared to mice which received CEA-specific T-cells #1175 as control.

The body weight of individual mice was weekly determined. We did not record any substantial alteration in the body weight of individual mice during the observation time. Moreover, no differences between the experimental groups were recorded.

2. No Toxicity Upon CAR #1138 Stimulation In Vivo

Figure 5:
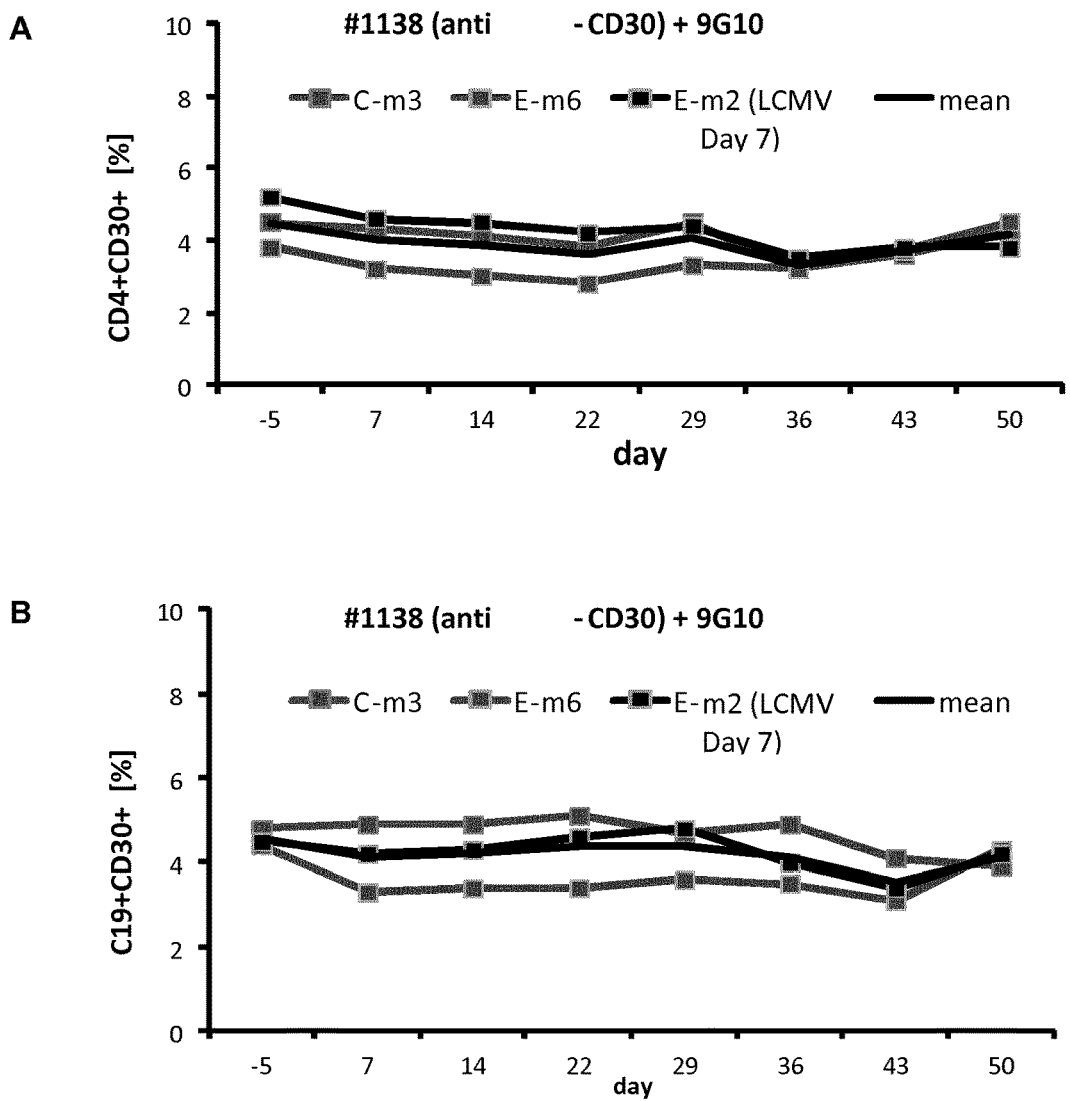
FIG. 5: $CD30^+$ T- and B-cells persist in the peripheral blood of humanized SCID mice in presence of anti-CD30 CAR T-cells #1138. SCID mice were engrafted with the human hematopoietic system to harbor human B- and T-cells in the peripheral blood. At day 0 human T-cells of the same donor and engineered with the #1138 CAR were adoptively transferred by i.v. injection. Peripheral blood $CD30^+$ $CD4^+$ T-cells (A) and $CD30^+$ $CD19^+$ B-cells (B) at day −5 before treatment and day +50 after treatment with anti-CD30 CAR T-cells #1138 were recorded by flow cytometry.

We challenged the anti-CD30 CAR T-cells #1138 in vivo by administration of irradiated 9G10 hybridoma cells which produce the anti-idiotypic antibody 9G10 directed against the HRS3 scFv domain of the CAR #1138. The antibody 9G10 is present on cell surface of the antibody producing cell and strongly activates engineered T-cells #1138 by CAR cross-linking. Under these test conditions the number of CD30$^+$CD4$^+$ T-cells or of CD30$^+$CD19$^+$ B-cells in the peripheral blood of treated mice was not altered (FIG. 5).

3. No Altered Immune Response after LCMV Infection as Test Pathogen

To explore whether the lymphocyte immune response against pathogens is altered in presence of T-cells #1138, the engrafted human immune system in Rag2$^{-/-}$ cγ$^{-/-}$ mice was challenged by infection with lympho-choriomeningitis virus (LCMV) at day 7 after adoptive therapy with T-cells #1138.

This assay is based on the fact that systemic LCMV infection in an immune competent host is controlled by specific CD8$^+$ and CD4$^+$ T-cells which become activated, produce an inflammatory infiltrate at the infection site and transiently express CD30 at high levels. Rag2$^{-/-}$ cγ$^{-/-}$ mice without transplanted T- and B-cell immune system cannot produce an anti-LCMV T-cell response. Humanized Rag2$^{-/-}$ cγ$^{-/-}$ mice with transplanted human immune system are asked whether they produce an inflammatory infiltrate after LCMV infection.

We challenged the immune response against LCMV by local virus application into the foot path. This is a classical infection assay to indicate the anti-virus immune response by swelling at the infection site within a few days.

We here recorded swelling of the foot path at the infection site as it is known for wild-type mice with full immune competence, e.g., balb/c mice. No loss of body weight was recorded in the experimental mouse treated by this route of infection. Data indicate that local LCMV infection is locally controlled in reconstituted Rag2$^{-/-}$ cγ$^{-/-}$ mice after therapy with anti-CD30 CAR T-cells #1138. No mouse died during the study.

However, a weight loss of about 30% (in average from 18 g to 12 g at day 10 vs day 27) was observed. Mice which received 9G10 antibody cells to stimulate the anti-CD30 T-cells #1138 controlled LCMV infection with less dramatic weight. For comparison, humanized Rag2$^{-/-}$ cγ$^{-/-}$ mice after therapy with anti-CEA T-cells #1175 did not show weight loss.

Data demonstrate that humanized mice with anti-CD30 T-cells #1138 are capable to conduct a cellular immune response upon LCMV infection indicated by foot path swelling in all cases. In mice treated with anti-CD30 T-cells #1138, however, response to LCMV infection may be associated with a moderate cytokine release syndrome due to acute T-cell #1138 activation leading to reduced food uptake and in weight loss. This is in contrast to mice which received the control T-cells with anti-CEA #1175 CAR which does not have a target in those mice and do not become activated.

4. Serum Pathology

Serum GOT (glutamic oxaloacetic transaminase) was recorded in mice of each experimental group and moreover in one mouse of each group which was systemically infected with LCMV. Serum GOT and GPT (glutamic-pyruvic transaminase) were determined by the Institut für Klinische Chemie, Uniklinik Köln, by using their SOPs. No significant changes in serum GOT levels were observed in treated mice during the observation period up to 57 days after T-cell therapy.

CONCLUSIONS

The toxicity of T-cells #1138 toward healthy autologous CD30$^+$ lymphocytes was tested in Rag2$^{-/-}$ cγ$^{-/-}$ mice fully reconstituted with the human hematopoietic system. T-cells from three donors were engineered with the anti-CD30 CAR #1138, as control with the anti-CEA CAR #1175, and tested for autoimmune reactivity towards the autologous healthy CD30$^+$ lymphocytes, in particular for the elimination of CD30$^+$ CD19$^+$ B-cells and CD30$^+$ CD4$^+$ T-cells. The total observation time for both the test and the control group was 60 days.

No signs of disease were recorded in treated mice. The frequency of CD30$^+$ CD19$^+$ B-cells and CD30$^+$ CD4$^+$ T-cells in the peripheral blood was not altered. The lack of signs of autoimmune toxicity was challenged by in vivo stimulation of engineered T-cells #1138 by application of the anti-idiotypic antibody 9G10 which binds to the binding domain of the CAR and induces CAR signalling and T-cell activation. No alteration in the frequency of CD30$^+$ CD19$^+$ B-cells and CD30$^+$ CD4$^+$ T-cells in the peripheral blood was observed.

The lymphocyte immune response against pathogens in humanized mice treated with anti-CD30 T-cells #1138 was not altered as shown by local infection with lymphochoriomeningitis virus (LCMV) at day 7 after transfer of T-cells #1138. Treated mice, however, suffered from a weight loss of about 30% (day 10 vs day 27). Since mice with transplanted T-cells #1175 did not show weight loss after LCMV infection we conclude that the anti-LCMV immune response in mice with T-cells #1138 produced a moderate cytokine release syndrome due to acute activation against CD30$^+$ target cells leading to less food uptake. No mouse died during infection.

Under the present test conditions adoptive therapy with T-cells #1138 preserved the B- and T-cell counts in peripheral blood and allowed a cellular immune protection against a test pathogen.

Example 3: Specific Expansion of #1138 CAR Modified T-Cells

Engineering of T-cells with CAR #1138 and #946

Engraftment of human peripheral T-cells with #1138 and for comparison #946 CAR, see Hombach A, et. Al., Gene Ther. 2010 October; 17(10):1206-13. doi: 10.1038/gt.2010.91. Epub 2010 Jun. 17, harbouring a CEA-specific scFv binding domain CEA was assessed by two colour FACS after 12 hrs after transduction. The initial efficiency was 29% for #1138 CAR and 22% for #946 CAR T-cells, respectively.

Monitoring T-Cells with CAR #1138 and #946

Figure 6:
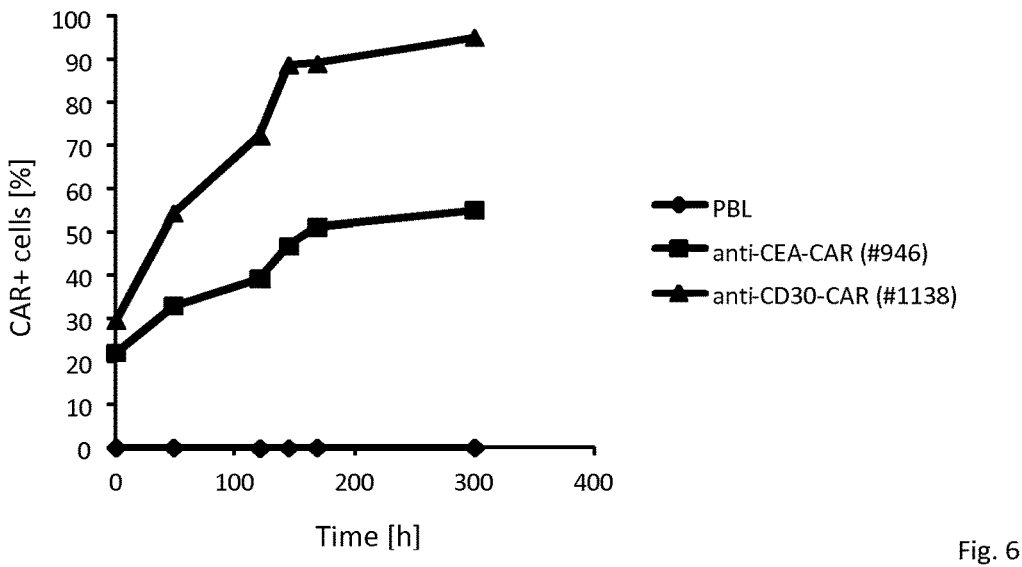
FIG. 6: T-cells with anti-CD30 CAR #1138 preferentially accumulate during in vitro culture. Peripheral blood lymphocytes were engrafted with the respective CARs. After transduction cells were cultured in Xvivo15 medium supplemented with 10% FCS and IL-2 (500 U/ml). Medium was replaced once a week, IL-2 was added every 3rd day. $CD3^+$ T-cells were recorded for CAR expression utilizing FITC-conjugated anti-mouse and PE-conjugated anti-human IgG1 Fc antibodies at the indicated time after start of culture.

After transduction cells were cultured in Xvivo15 medium supplemented with 10% FCS and IL-2 (500 U/ml). Medium was replaced once a week, IL-2 was added every 3rd day. A sample of cells was removed at different time points and CD3+ T-cells were analyzed for CAR expression utilizing FITC-conjugated anti-mouse and PE-conjugated anti-human IgG1 Fc antibodies. Data are summarized in FIG. 6.

CONCLUSIONS

The number of #1138 CAR T-cells increased substantially during extended cultivation up to 300 h compared with #946 CAR T-cells and resulted in >90% of all T-cells with #1138 CAR compared to 50% T-cells with #946 CAR.

Example 4: Specific Cytolysis of B-Cells

As shown in FIG. 7a, B-cells were isolated from PBMC according to standard procedures. In addition, T-cells were isolated from PBMC, grafted with CAR #1138, CFSE-labeled and separated into CAR+ and CAR− populations. The autologous B-cells were activated for 96 h by sCD40L/IL-4 according to standard procedures, labelled with PKH26 and sorted into CD30+ and CD30− populations by flow cytometry based cell sorting. Labelled T-cells were co-cultivated (2.5×10⁴/well) for 24 h with B-cells, recovered, stained with 7-AAD and analysed by flow cytometry. For control, target cell lysis of Myla cells representing malignant T-cells was determined by a XTT-based viability assay. As shown in FIG. 7B, there is no significant cytolysis of CD19+ B-cells by CAR+ or CAR− T-cells whereas a substantial cytolysis of CD30+ Myla cells occurred when co-incubated with #1138 CAR T-cells. Moreover, there is no substantial difference in cytolysis of CD30+ and CD30− cells of the CD19+ B-cells by CAR #1138 T-cells compared to T-cells without CAR.

The invention claimed is:

1. A method of adoptive cell therapy for treating CD30$^+$ cancer in a subject in need thereof comprising the step of administering to said subject a T-cell with a chimeric antigen receptor whereby the chimeric antigen receptor contains at least the following domains starting from the N-terminus to the C-terminus: an anti-CD30 single chain antibody domain, comprising an HRS3 scFv peptide having the sequence as set forth in SEQ ID NO: 2, optionally a spacer domain, a transmembrane domain derived from CD28, and a cytoplasmatic signaling domain, wherein the cytoplasmic signaling domain is a CD28 endodomain lacking the lck binding motif, having the sequence as encoded by SEQ ID NO: 6 and wherein said T-cell with the chimeric antigen receptor is toxic to CD30$^+$ cancer cells, while being non-toxic to CD30$^+$ non-cancer activated T-cells, B-cells and/or stem cells in said subject, and wherein said CD30$^+$ cancer cells include one or more of CD30$^+$ leukemia cells and CD30$^+$ lymphoma cells.

2. The method for adoptive cell therapy for treating CD30$^+$ cancer in a subject in need thereof according to claim 1, wherein the T-cell with a chimeric antigen receptor further comprises a leader sequence located N-terminally to the anti-CD30 single chain antibody domain.

3. The method for adoptive cell therapy for treating CD30$^+$ cancer in a subject in need thereof according to claim 1 wherein the spacer domain is an IgG1 CH2CH3 domain having the sequence as set forth in SEQ ID NO: 0.5.

4. The method of claim 1, wherein the spacer domain is a mutated IgG$_1$ hinge-CH2CH3 domain having the sequence as set forth in SEQ ID NO: 10.

5. The method for adoptive cell therapy for treating CD30$^+$ cancer in a subject in need thereof according to claim 1 wherein the cytoplasmic signaling domain is an intracellular domain selected from the group consisting of a CD3 zeta signaling domain, a Fc epsilon receptor gamma signaling chain and a costimulatory domain.

6. The method of claim 5, wherein the intracellular domain is the CD3 zeta signaling domain having a sequence as encoded by SEQ ID NO: 7, or wherein the intracellular domain is the Fc epsilon receptor gamma signaling chain having a sequence as encoded SEQ ID NO:8.

7. A method for adoptive cell therapy for treating CD30$^+$ cancer in a subject in need thereof, comprising the step of administering to said subject a T-cell with a chimeric antigen receptor whereby the chimeric antigen receptor contains at least the following domains starting from the N-terminus to the C-terminus:
an anti-CD30 single chain antibody domain,
optionally a spacer domain,
a transmembrane domain, and
a cytoplasmatic signaling domain, wherein the cytoplasmic signaling domain is a CD28 endodomain lacking the lck binding motif, having the sequence as encoded by SEQ ID NO: 6, and
wherein said T-cell with the chimeric antigen receptor is toxic to CD30$^+$ cells of a cancer selected from the group consisting of Hodgkin's lymphoma, non-Hodgkin's B cell lymphoma, mycosis fungoides, Sézary lymphoma, anaplastic large cell lymphoma, acute lvmphocytic leukaemia, cutaneous lymphoma, lymphoproliferative diseases, systemic mastocytosis, teratocarcinoma, stem cell-derived malignancies, B-cell lymphoma and T-cell lymphoma, while being non-toxic to CD30$^+$ non-cancer activated T-cells, B-cells and/or stem cells in said subject, and
wherein the chimeric antigen receptor is a polypeptide having the sequence as set forth in SEQ ID NO: 3.

8. The method for adoptive cell therapy for treating CD30$^+$ cancer in a subject need thereof according to claim 1 wherein the CD30$^+$ cancer is any one of Hodgkin's lymphoma, anaplastic large cell lymphoma, acute lymphocytic leukaemia, cutaneous lymphoma, mycosis fungoides, lymphoproliferative diseases, systemic mastocytosis, teratocarcinoma, stem cell derived malignancies, cancer stem cells.

9. The method for adoptive cell therapy for treating CD30$^+$ cancer in a subject is need thereof according to claim 1 wherein the CD30$^+$ cancer is a B-cell lymphoma or a T-cell lymphoma.

10. The method of adoptive cell therapy for treating CD30$^+$ cancer in a subject in need thereof according to claim 1 wherein the CD30$^+$ cancer is selected from the group consisting of Hodgkin's lymphoma, non-Hodgkin's B cell lymphoma, mycosis fungoides or Sézary lymphoma.

* * * * *